United States Patent
Brown et al.

(10) Patent No.: US 11,523,935 B2
(45) Date of Patent: Dec. 13, 2022

(54) COMPRESSIBLE VAGINAL PESSARY FOR TREATMENT OF STRESS URINARY INCONTINENCE

(71) Applicant: Wisconsin Alumni Research Foundation, Madison, WI (US)

(72) Inventors: Heidi W. Brown, Monona, WI (US); Rachel J. Craven, Madison, WI (US); Alexandra M. Hadyka, Selbyville, DE (US); Julia M. Handel, Madison, WI (US); Kathryn M. Hohenwalter, Brookfield, WI (US); Gloria E. Sarto, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 110 days.

(21) Appl. No.: 16/859,248

(22) Filed: Apr. 27, 2020

(65) Prior Publication Data
US 2020/0337889 A1    Oct. 29, 2020

Related U.S. Application Data

(60) Provisional application No. 62/839,029, filed on Apr. 26, 2019.

(51) Int. Cl.
*A61F 6/08* (2006.01)
*A61L 27/16* (2006.01)

(52) U.S. Cl.
CPC .............. *A61F 6/08* (2013.01); *A61L 27/165* (2013.01)

(58) Field of Classification Search
CPC ...... A61F 2/02; A61F 6/08; A61F 6/12; A61F 6/14; A61F 6/142; A61F 6/144; A61F 6/146; A61F 6/148; A61F 6/16; A61F 6/18; A61F 2/0004; A61F 2/0009; A61F 2/0013; A61F 2/0022; A61F 2/0027; A61F 2/0031; A61F 2/0036; A61F 2/004; A61F 2/005;

(Continued)

(56) References Cited

U.S. PATENT DOCUMENTS 6,645,137 B2 *  11/2003  Ulmsten ................. A61F 2/005
                                                   128/834
7,717,892 B2 *  5/2010   Bartning ................ A61F 6/08
                                                   604/15

(Continued)

OTHER PUBLICATIONS

Davis et al., Digital and Mechanical Characterization of Ureteral Stent Luminal Reduction in Response to Extrinsic Compression Force, 2018, [retreived Oct. 5, 2021 from https://www.liebertpub.com/doi/pdf/10.1089/end.2018.0573 [Online], Journal of Endourology, vol. 32, No. 12 (Year: 2018).*

(Continued)

*Primary Examiner* — Ophelia A Hawthorne
*Assistant Examiner* — Gina McCarthy
(74) *Attorney, Agent, or Firm* — Boyle Fredrickson S.C.

(57) ABSTRACT

The present invention provides a vaginal pessary that offers mid-urethral support and is anchored proximate the cervix by a proximal annulus engaging opposing walls of the vagina and supporting a distal annulus engaging opposing walls of the vagina posterior to the mid-urethra. The proximal and distal annulus are joined by compressible cross rods compressible to reduce a diameter of at least one of the proximal and distal annuli.

17 Claims, 2 Drawing Sheets

(58) Field of Classification Search
CPC ....... A61F 5/449; A61D 9/02; A61B 17/0482; A61B 10/0045
See application file for complete search history.

(56) References Cited

U.S. PATENT DOCUMENTS

| | | | | |
|---|---|---|---|---|
| 2008/0281149 | A1* | 11/2008 | Sinai | A61F 2/005 600/32 |
| 2009/0203959 | A1* | 8/2009 | Ziv | A61F 2/005 600/29 |
| 2011/0065980 | A1* | 3/2011 | Ziv | A61F 2/005 600/30 |
| 2012/0041465 | A1* | 2/2012 | Shalon | A61B 17/0482 606/191 |
| 2012/0259162 | A1 | 10/2012 | Karapasha | |
| 2017/0360594 | A1* | 12/2017 | Park | A61F 5/449 |
| 2019/0282350 | A1* | 9/2019 | Conti | A61B 10/0045 |

OTHER PUBLICATIONS

Scott A. Farrell et al.; Effectiveness of a new self-positioning pessary for the management of urinary incontinence in women; Research Paper; American Journal of Obstetrics & Gynecology May 2007;pp. 474.e1-474.e8.

Poise Impressa; Screen Shot of Web-Site—http://www.poise.com/products/impressa.

* cited by examiner

COMPRESSIBLE VAGINAL PESSARY FOR TREATMENT OF STRESS URINARY INCONTINENCE

CROSS-REFERENCE TO RELATED APPLICATIONS

This application claims the benefit of U.S. Provisional Application No. 62/839,029, filed Apr. 26, 2019, and hereby incorporated by reference.

STATEMENT REGARDING FEDERALLY SPONSORED RESEARCH OR DEVELOPMENT

BACKGROUND OF THE INVENTION

The present invention relates to vaginal pessaries for treating stress urinary incontinence.

Accidental urinary leakage affects more than half of independent women aged 65 and older in the United States. Stress urinary incontinence is the most prevalent type of urinary incontinence, present in over 80% of urinary incontinence cases. Stress urinary incontinence is defined by leakage associated with activities that increase intra-abdominal pressure, such as when coughing, sneezing, and during physical activity. Pelvic floor muscle strengthening, vaginal pessaries, and mid-urethral sling surgery are common treatment options for those suffering from stress urinary incontinence.

Pelvic floor muscle strengthening exercises are done by flexing the muscles used to stop urination. When exercises are maintained, pelvic floor muscle strengthening exercises are shown to be effective in treating stress urinary incontinence in just over half of women in the short term. However, many women discontinue their exercises over time.

Pessaries are vaginally inserted devices that are used to treat pelvic organ prolapse as well as urinary incontinence. Current pessaries for treating urinary incontinence are commonly ring-shaped devices with a knob at the distal end, placed with the proximal end of the ring against the cervix or the apex of the vagina and the more distal end (with the knob) against the pubic symphysis on the anterior vaginal wall. The more distal end with the knob is intended to support the area beneath the bladder neck. Current vaginal pessaries operate on the belief that loss of support of the bladder neck contributes to the cause of stress urinary incontinence. Current pessaries are shown to improve the symptoms of about half of women.

Through a better understanding of the underlying pathophysiology of stress urinary incontinence, it has been found that support of the mid-urethra, not just the bladder neck, may be important for treating stress urinary incontinence. Mid-urethral sling surgery draws on this idea by using a synthetic mesh to provide "sling" support underneath the mid-urethra where the weakened pelvic floor muscles previously provided support. Mid-urethral sling surgery has proven to be the most effective treatment so far for treating stress urinary incontinence, resulting in improvement in over 90% of women who undergo the surgery.

Despite the success of mid-urethral sling surgery, the surgery may not be an available option to all women and others may not wish to undergo the invasive surgery.

SUMMARY OF THE INVENTION

The present inventors have recognized that it is possible to produce a vaginal pessary that offers appropriate mid-urethral support. The new vaginal pessary provides a larger proximal annulus that anchors the pessary device within the vagina toward the cervix and is separated in parallel planes by an X-shaped frame from a smaller distal annulus extending toward the opening of the vagina to be positionable posterior to the mid-urethra to provide posterior support behind the urethra.

It is thus a feature of at least one embodiment of the present invention to allow easy insertion and removal of the pessary from the vagina without physician assistance by placement of the distal annulus close to the vaginal opening whereby compression of the distal annulus by the patient compresses the entire width of the pessary.

It is also a feature of at least one embodiment of the present invention to prevent longitudinal movement of the pessary along an axis of the vagina by using a larger proximal annulus engaging the vaginal walls perpendicular to the axis to anchor the pessary to the vaginal walls.

In one embodiment, the present invention is a pessary device for treating stress urinary incontinence having a first annulus elastically deformable to bend inward and providing an outward radial force configured to engage opposing walls of the vagina; a second annulus elastically deformable to bend inward and providing an outward radial force configured to engage opposing walls of the vagina and having a diameter less than the first annulus; and first and second rods intersecting at a pivot point and having ends of the first and second rods separated by attachment to opposite ends of the first and second annulus, respectively, wherein the first and second rods are compressible toward each other about the pivot point to further reduce a dimension of at least one of the first and second connected annulus.

It thus a feature of at least one embodiment of the present invention to place sufficient localized pressure on the mid-urethra to prevent urine leakage associated with stress urinary incontinence.

A length of the first and second rods may be between 4 cm and 9 cm.

It thus a feature of at least one embodiment of the present invention to position the proximal ring near the cervix and the distal ring posterior to the mid-urethra in an average sized human patient's vagina.

A diameter of the first annulus may be between 3 cm and 6 cm and a diameter of the second annulus is between 1 cm and 3 cm.

It thus a feature of at least one embodiment of the present invention to anchor the proximal ring deeper within the vagina to prevent the pessary from becoming dislodged during user movement while the distal ring sits comfortably near the opening of the vagina where the ring may be easily reached by the patient.

The first and second annulus may provide a flexure reducing a diameter of the first and second annulus in at least one direction such that the first annulus and second annulus may be sized to be inserted into the vagina.

It thus a feature of at least one embodiment of the present invention to allow the pessary to be easily insertable by the patient without physician or medical professional intervention in an at-home environment and without having to go into a medical office or hospital.

The first and second annulus may be rings of silicone rubber. The rings may have a cross sectional thickness between 0.25 cm and 1 cm.

It thus a feature of at least one embodiment of the present invention to allow the biocompatible rings to be sterilizable for repeated use.

The first and second annulus may provide a flexure reducing a diameter of the pessary at least 50% under less than 40 Newton force.

It thus a feature of at least one embodiment of the present invention to permit older or weaker patients to compress the ring(s) of the device with a single hand for insertion and removal from the vagina.

The pivot point of the first and second rods may be closer to the second annulus than the first annulus.

It thus a feature of at least one embodiment of the present invention to utilize a double lever of the first class to produce greater compression of the larger proximal ring through a smaller compression on the smaller distal ring using a longer load arm of the proximal ring.

The first and second rods may be rigid wires coated with silicone rubber.

It thus a feature of at least one embodiment of the present invention to allow the elastic rods to quickly rebound after being compressed to stabilize the device within the vagina and to prevent sliding along the vagina.

The first and second rods may be compressible at least 50% toward each other under less than 40 Newton force.

It thus a feature of at least one embodiment of the present invention to produce a fulcrum at the intersection of the rods that allow the proximal and distal rings to compress about the fulcrum with minimal force by the patient.

In an alternative embodiment, the present invention is a method of treating stress urinary incontinence including the steps of: providing a pessary having a first annulus dimensioned to extend across opposing walls of a vagina opposite a second annulus dimensioned to extend across opposing walls of a vagina and having a diameter less than the first annulus, the first and second annulus joined by separated first and second ends of a pair of cross rods, respectively, intersecting at a pivot point and compressible toward each other to further compress at least one of the attached first and second annulus; compressing at least one of the first annulus, second annulus and pair of cross rods to reduce a width of the pessary to allow insertion of the pessary into the vagina; inserting the pessary such that the first annulus is proximate a cervix and the second annulus is proximate an opening of the vagina posterior to the mid-urethra; and releasing the at least one of the first annulus, second annulus and pair of cross rods to allow the first and second annulus to contact the opposing walls of the vagina.

The second annulus may be positionable posterior to the mid-urethra to provide an opposing force when pressure is applied to the mid-urethra.

Compression of the opposed ends of the pair of cross rods toward each other further compress the joined first and second annulus.

These particular objects and advantages may apply to only some embodiments falling within the claims and thus do not define the scope of the invention.

DETAILED DESCRIPTION OF THE INVENTION

Figure 1:
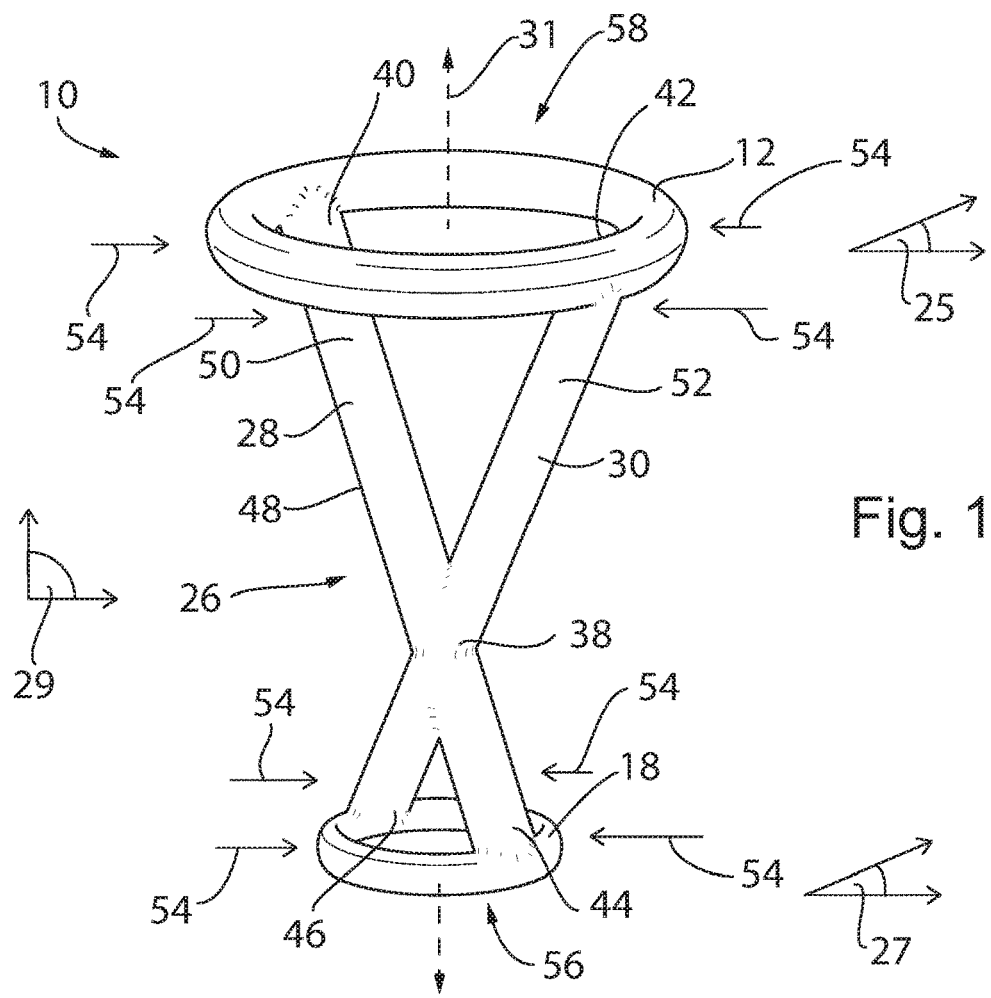
FIG. 1 is a perspective view of a pessary of the present invention shown in partial phantom and providing an elastomeric first and second annulus supported coaxially in separate parallel planes by compressible cross bars having internal support wires.
Figure 2:
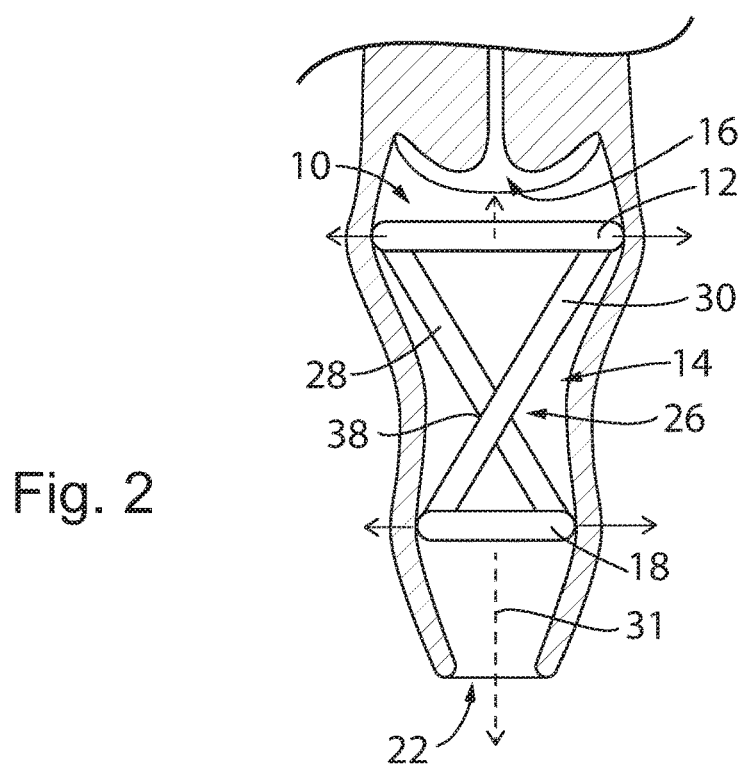
FIG. 2 is a cross-section of the vagina taken along a coronal plane extending between a patient's anterior and posterior sides and showing the first annulus anchored to the inner walls of the vagina proximate the cervix to retain the second annulus in position proximate the opening of the vagina posterior to the mid-urethra.
Figure 3:
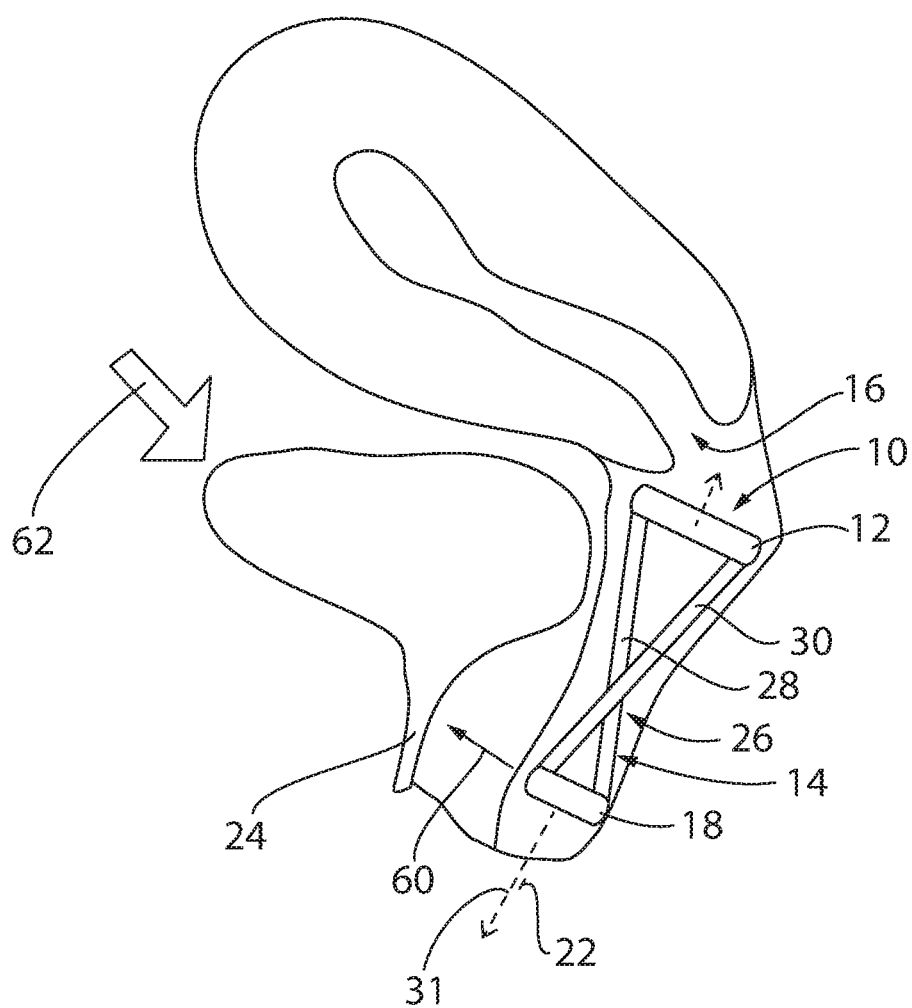
FIG. 3 is a cross-section of a vagina taken along a sagittal plane extending between a patient's left and right sides and showing the pessary inserted into the vagina with the first annulus positionable proximate the cervix and the second annulus positionable proximate the opening of the vagina, and the second annulus providing support to the mid-urethra in response to intra-abdominal pressures applied to the vaginal region.

Referring now to FIGS. 1 through 3, a pessary 10 may include a large annulus 12 positionable desirably positionable proximate a proximal end of a vagina 14 toward a cervix 16 opposite a small annulus 18 desirably positionable proximate to the distal end of the vagina 14 toward an opening 22 of the vagina 14 and generally posterior to a midsection of the urethra 24. The large annulus 12 and the small annulus 18 may be supported coaxially in separated parallel planes 25, 27 by an X-shaped frame 26 lying generally within a plane 29 extending along an axis of separation 31 extending between the large annulus 12 and small annulus 18.

The X-shaped frame 26 has a first straight beam 28 intersecting a second straight beam 30. Opposed ends of the first straight beam 28 and second straight beam 30 are attached to the large annulus 12 at diametrically opposed locations and to the small annulus 18 at diametrically opposed locations, respectively, to space the large annulus 12 from the small annulus 18 along the axis of separation 31, which is perpendicular to the planes 25, 27 of the large annulus 12 and small annulus 18 to position the large annulus 12 and small annulus 18 at desired anatomical locations within the vagina 14 as further described below.

Referring now to FIG. 1, the X-shaped frame 26 may include the first straight beam 28 and the second straight beam 30 joined and intersecting and/or overlapping at a pivot point 38 forming a fulcrum, similar to a scissors, whereby the first straight beam 28 and second straight beam 30 may bend or compress about the pivot point 38. The first straight beam 28 and second straight beam 30 may extend from the parallel planes 25, 27 at angles between approximately 60-80 degrees and extend within the plane 29 of the X-shaped frame 26.

The first straight beam 28 and the second straight beam 30 may have upper ends 40, 42, respectively, opposite of lower ends 44, 46, respectively. The upper ends 40, 42 may correspond to attachment of the large annulus 12 while the lower ends 44, 46 may correspond to attachment of the small annulus 18 as further described below. The first straight beam 28 and the second straight beam 30 may intersect such that the pivot point 38 is positioned closer to the lower ends 44, 46 as compared to the upper ends 40, 42 to provide a smaller distance between the lower ends 44, 46 corresponding to a smaller diameter of the small annulus 18 and a larger distance between the upper ends 40, 42 corresponding to a larger diameter of the large annulus 12.

The first straight beam 28 and second straight beam 30 may compress toward each other about the pivot point 38 in a pivoting, scissors-like manner in which compression of the upper ends 40, 42 translates to compression of the lower ends 44, 46 and vice versa. This mechanism allows the patient to compress one of the upper ends 40, 42 and lower ends 44, 46 of the first straight beam 28 and second straight beam 30 thus resulting in the opposite ends to also compress.

The X-shaped frame 26 may be an injection molded elastomer 48 such as medical grade silicone, silicone rubber, rubber or the like. The elastomer 48 may have a stiffness between 30-70 durometer. The first straight beam 28 and second straight beam 30 may be the same length and may be between 4 cm and 9 cm in length, and at least 6 cm, and at least 7 cm, and at least 8 cm in length.

Extending within the elastomer 48 of each of the first straight beam 28 and second straight beam 30, along a longitudinal axis of the beams proximate a center of the cross section of the beams, may be rigid internal support wires 50, 52, respectively, increasing the rigidity of the first straight beam 28 and second straight beam 30 and further facilitating the scissors-like movement of the X-shaped frame 26. The internal support wires 50, 52 may be stainless-steel wires, for example 20-gauge stainless steel wires. The internal support wires 50, 52 may be between 4 cm and 9 cm in length, and at least 6 cm, and at least 7 cm, and at least 8 cm in length and generally correspond to and extend along a length of the first straight beam 28 and second straight beam 30 respectively. The wires 50, 52 may be overlapping within the elastomer 48 and separated by about 0.02 mm or about 0.01-0.03 mm at the pivot point 38 due to intervening elastomer 48.

A cross-section of each of the first straight beam 28 and second straight beam 30 may take the form of a circle or oval cross-section having a diameter of between 0.25 cm and 1.5 cm and less than 1.5 cm and less than 1 cm and less than 0.5 cm and about 0.5 cm to provide the necessary strength yet facilitate a desired compressibility of the frame material. The first straight beam 28 and second straight beam 30 may also have a cross-section of other known shapes such as square and rectangle.

It is understood that the elastomer 48 and internal support wires 50, 52 of the first straight beam 28 and second straight beam 30 allow the X-shaped frame 26 to compress inward when pinching forces 54 are applied to upper ends 40, 42 or lower ends 44, 46 of the X-shaped frame 26 while rebounding back to its original form when the force is released. The resilience and elasticity of the elastomer 48 allows for repeated flexing without losing its ability to rebound back to its original shape and size.

The X-shaped frame 26 may have a flexure reducing the distance between the upper ends 40, 42, respectively, or lower ends 44, 46, respectively, by at least 50% under a force less than 40 N, which has been identified as the average maximum pinch force that patients with limited dexterity can apply. In this respect the X-shaped frame 26 may be compressed with a low threshold manual force.

The upper ends 40, 42 of the X-shaped frame 26 may be attached to the large annulus 12 at diametrically opposed ends of the large annulus 12. In this respect a distance between the upper ends 40, 42 may generally correlate to a diameter of the large annulus 12.

The large annulus 12 may be a ring having an outer diameter between 3.5 cm and 4.5 cm and at least 3.5 cm and at least 3.8 cm and at least 4.0 cm and about 4.0 cm in a relaxed state to be sized to engage an inner wall of a proximal end of the vagina 14 proximate the cervix 16 in an anchoring manner as further described below.

A cross-section of the large annulus 12 may be a circle or oval cross-section having a diameter between 0.25 cm and 1.5 cm and less than 1.5 cm and less than 1 cm and less than 0.5 cm and about 0.5 cm to provide a desired compressibility. The cross-section of the large annulus 12 is generally formed of a smooth or curved outer perimeter increasing the comfort of the contact between the large annulus 12 and the inner wall of the vagina 14. The smooth outer surface of the large annulus 12 also prevents scarring or tearing of the vagina 14.

The large annulus 12 may be an injection molded elastomer such as medical grade silicone, silicone rubber, rubber or the like. The elastomer may have a stiffness between 30-70 durometer. The elastomer allows the material to flex inward when pinching forces 54 are applied to opposite ends of the large annulus 12 while rebounding back to its original form when the force 54 is released. The resilience of the elastomer allows for repeated flexing without losing its ability to rebound back to its original shape and size.

The large annulus 12 may have a flexure reducing the diameter of the large annulus 12 in at least one direction by at least 50% under a force less than 40 N, which has been identified as the average maximum pinch force that patients with limited dexterity can apply. In this respect the large annulus 12 may be compressed under a low threshold pinch force while still providing sufficient resistance or rebounding force to engage the inner wall of the vagina 14.

The lower ends 44, 46 of the X-shaped frame 26 may be attached to the small annulus 18 at diametrically opposed ends of the small annulus 18. In this respect a distance between the lower ends 44, 46 may generally correlate to a diameter of the small annulus 18.

The small annulus 18 may be a ring having an outer diameter of between 1.5 cm and 2.5 cm and at least 1.5 cm and at least 2 cm and about 2 cm to be sized in a relaxed state to engage an inner wall of a distal end of the vagina 14 proximate the opening 22 of the vagina 14 in a supportive manner posterior to the mid-urethra 24 as seen in FIG. 3 and further described below.

A cross-section of the small annulus 18 may be a circle or oval having a diameter of between 0.25 cm and 1.5 cm and less than 1.5 cm and less than 1 cm and less than 0.5 cm and about 0.5 cm to facilitate a desired compressibility. The cross-section of the small annulus 18 is generally formed of a smooth or curved outer perimeter increasing the comfort of the contact between the small annulus 18 and the inner wall of the vagina 14. The smooth outer surface of the small annulus 18 also prevents scarring or tearing of the vagina 14.

The small annulus 18 may be an injection molded elastomer such as medical grade silicone, silicone rubber, rubber or the like. The elastomer may have a stiffness between 30-70 durometer. The elastomer allows the material to flex inward when pinching forces 54 are applied to opposite ends of the small annulus 18 while rebounding back to its original form when the force is released. The resilience of the elastomer allows for repeated flexing without losing its ability to rebound back to its original shape and size.

The small annulus 18 may have a flexure reducing the diameter of the small annulus 18 in at least one direction by at least 50% under a force less than 40 N which has been identified as the average maximum pinch force that patients with limited dexterity can apply. In this respect the small annulus 18 may be compressed under a low threshold pinch force while still providing sufficient resistance or rebounding force to engage the inner wall of the vagina 14.

Referring also to FIG. 2, the large annulus 12 and the small annulus 18 may be spaced apart by the X-shaped frame 26 to be positionable within the vagina 14 at desired anatomical positions. The pessary 10 may have a total length, measured along the axis of separation 31, between 4 cm and 10 cm and at least 5 cm and at least 6 cm and at least 7 cm and at least 8 cm and about 8 cm. The length of the pessary 10 may approximate an average length of the vagina 14 between a position just below the cervix 16 and a position within the vagina posterior to the mid-urethra 24. A shortened length may be used to accommodate a shortened vaginal length after hysterectomy in postmenopausal patients.

A greatest width of the pessary 10 may be defined by the diameter of the large annulus 12 which is sized to engage a greatest diameter of the vagina 14 to provide a supportive anchoring or "foothold" to the wall of the vagina 14 and to prevent longitudinal movement of the pessary 10. It is understood that the large annulus 12 may engage a slightly widened proximal end of the vagina 14 as the vagina 14 approaches the cervix 16.

The diameter of the small annulus 18 is generally smaller than the large annulus 12 and sized to support a narrower diameter of the vagina 14 proximate the opening 22 of the vagina 14. For example, the diameter of the small annulus 18 may be 30% to 60% smaller than the large annulus 12. Although the small annulus 18 is intended to provide some anchoring functions, the smaller diameter of the small annulus 18 desirably fits comfortably within the vagina 14 in a supporting manner behind the mid-urethra 24.

It is understood that the sizing of the pessary 10, for example, the length and width of the pessary 10, and diameters of the large annulus 12 and small annulus 18 will depend on the size of the vagina 14 of the patient and may be fitted according to each patient's dimensions.

Exemplary dimensions of the pessary 10 are shown below in Table 1, for example, having two different sizes, i.e., "short" and "long", to accommodate varying anatomical sizes of the patient. It is contemplated that at least five different sizes of pessary 10 may be manufactured to accommodate different vagina 14 sizes.

TABLE 1

| Feature | Short | Long |
| --- | --- | --- |
| Large Ring Diameter | 3.5 cm | 4 cm |
| Small Ring Diameter | 2 cm | 2 cm |
| Device (silicone) Thickness | 0.5 cm | 0.5 cm |
| Length | 5 cm | 8 cm |
| Volume Silicone | 5 mL | 6 mL |

It is understood that the X-shaped frame 26, the large annulus 12, and small annulus 18 may be injection molded in a single mold as an integral or unitary piece in order to eliminate any breaks or seams between respective parts which may cause dirt or debris to enter the pessary 10, and eliminating the need to attach the X-shaped frame 26 to the large annulus 12 and small annulus 18 after injection molding the separate parts. The internal support wires 50, 52 may be molded within the elastomer 48 with the assistance of cured silicone squares to center the ends of the support wires 50, 52 within the mold. The elastomer 48 is then injected into the mold and then the mold is heat cured. Additional curing of the pessary 10 and sterilization is completed before use by patients.

Referring now to FIGS. 2 and 3, when the pessary 10 is in use by the patient, the patient may compress a distal end 56 of the pessary 10 proximate the small annulus 18 and desirably positionable at a distal end of the vagina 14, whereby compression is translated to a proximal end 58 of the pessary 10 proximate the large annulus 12 and desirably positionable at a proximal end of the vagina 14.

The patient may apply a compression force 54 on the small annulus 18 by pinching opposite ends of the small annulus 18. The patient may also apply a compression force 54 to the lower end of the X-shaped frame 26 by pinching the lower ends 44, 46 together in a similar manner. The compression of the distal end 56 may be done manually without tools and with a single hand without physician assistance. The compression force 54 is translated to the upper ends 40, 42 and the large annulus 12 to compress the large annulus 12. The simultaneous compression of the small annulus 18, X-shaped frame 26, and large annulus 12 therefore provides an outer dimension or greatest width of the pessary 10 that is reduced in at least one direction whereby the pessary 10 may be more easily inserted into the vagina 14 by the patient.

The patient may insert the pessary 10 through the opening 22 of the vagina 14 with the large annulus 12 entering the vagina 14 first, followed by the X-shaped frame 26, and lastly followed by the small annulus 18. The desired positioning of the pessary 10 places the small annulus 18 between 1 cm and 2 cm inward from the opening 22 of the vagina 14 or between 1 cm and 2 cm below a protrusion of the vagina 14 formed by the pubic bone. This location of the small annulus 18 positions the posterior support of the pessary 10 substantially behind and slightly below the mid-urethra 24. By virtue of the placement of the small annulus 18 and the length of the X-shaped frame 26, the large annulus 12 is positionable at the proximal end of the vagina 14 proximate the cervix 16.

Once the pessary 10 is inserted to the desired depth within the vagina 14, the patient may release the compression force 54 on the small annulus 18 and/or the X-shaped frame 26 so that the small annulus 18, X-shaped frame 26 and large annulus 12 rebound back to their relaxed states within the vagina 14.

In the relaxed state the large annulus 12 may provide an outward radial force against the inner walls of the vagina 14 thus "anchoring" the large annulus 12 to the vagina 14. In this respect the large annulus 12 may prevent or reduce the longitudinal movement of the pessary 10 along the vagina 14 preventing the pessary 10 from dislodging from the vagina 14 occurring, for example, during patient movement. The radial distributed contact of the large annulus 12 about a perimeter of the inner walls of the vagina 14 distributes the pressure placed on the inner walls of the vagina 14 to minimize discomfort to the patient.

Referring to FIG. 3, the expansion of the small annulus 18 to the relaxed state further provides an outward radial force against the inner walls of the vagina 14 providing an opposing force 60 against intra-abdominal pressures 62 placed on the mid-urethra 24. In this position the small annulus 18 acts as a backstop to passively support the mid-urethra 24 underneath the urethra when intra-abdominal pressures 62 place downward forces on the mid-urethra 24 such as during physical activity.

When the patient desires to remove the pessary 10, the patient may reach into the vagina 14 and locate the small annulus 18 proximate the opening 22 of the vagina 14 and apply a compression force 54 on the small annulus 18 and/or the lower end of the X-shaped frame 26 to translate further compression of the large annulus 12 and to the pessary 10 out of the vagina 14.

It is contemplated that the pessary 10 may be made of a material that is biocompatible, easy to clean (sterile) for repeated use, and safe for medical applications. The pessary may be able to withstand an internal body temperature of about 98.6 degrees Fahrenheit. The pessary 10 may weigh less than 10 grams.

It is also contemplated that the pessary 10 may be durable enough to be used repeatedly daily (for at least 12 hours) and to be taken out at night, for a duration of at least ninety days. The pessary 10 may be reused for at least 5 years without significant wear and tear.

The pessary 10 may be able to stop at least 60% and at least 90% of urine leakage during an episode of incontinence.

"Anterior" refers to the front of the human body, and "posterior" refers to the back of the human body.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A pessary device insertable into a vagina along an insertion axis for treating stress urinary incontinence comprising:
    a first annulus defining an outermost dimension perpendicular to the insertion axis of a first end of the pessary device and elastically deformable to bend inward and provide an outward radial force configured to engage opposing walls of the vagina;
    a second annulus defining an outermost dimension perpendicular to the insertion axis of a second end of the pessary device and elastically deformable to bend inward and provide an outward radial force configured to engage opposing walls of the vagina; and
    an elastic bridge connected between the first annulus and the second annulus and compressible to reduce the outermost dimension of at least one of the first and second connected annulus;
    wherein the elastic bridge comprises first and second intersecting rods having upper ends attached at diametrically opposite ends of the first annulus and lower ends attached to diametrically opposite ends of the second annulus wherein the first and second intersecting rods intersect at a pivot point configured to bring the upper ends closer together when the lower ends are brought closer together to reduce the outermost dimension of the first annulus when the outermost dimension of the second annulus is reduced.

2. The pessary device of claim 1 wherein an uncompressed diameter of the second annulus is less than the first annulus.

3. The pessary device of claim 2 wherein the diameter of the first annulus is between 3 cm and 6 cm and a diameter of the second annulus is between 1 cm and 3 cm.

4. The pessary device of claim 1 wherein the first and second annulus provide a flexure reducing a diameter of the first and second annulus in at least one direction such that the first annulus and second annulus may be sized to be inserted into the vagina.

5. The pessary device of claim 4 wherein the first and second annulus are rings of silicone rubber.

6. The pessary device of claim 5 wherein the first and second annulus have a cross sectional diameter between 0.25 cm and 1 cm.

7. The pessary device of claim 1 wherein the first and second annulus provides a flexure reducing a width of the pessary at least 50% under less than 40 Newton force.

8. The pessary device of claim 1 wherein a length of the first and second intersecting rods is between 4 cm and 9 cm.

9. The pessary device of claim 1 wherein the pivot point of the first and second rods is closer to the second annulus than the first annulus.

10. The pessary device of claim 1 wherein the first and second intersecting rods are rigid wires coated with silicone rubber.

11. The pessary device of claim 1 wherein the first and second intersecting rods are compressible at least 50% toward each other under less than 40 Newton force.

12. A method of treating stress urinary incontinence in a human patient, the method comprising the steps of:
    providing a pessary having a first annulus having an outermost dimension at a first end of the pessary configured to extend across opposing walls of a vagina opposite a second annulus having an outermost dimension at a second end of the pessary configured to extend across opposing walls of the vagina, the first and second annulus joined by an elastic bridge connected between the first annulus and the second annulus and compressible to reduce the outermost dimension of at least one of the first and second connected annulus wherein the elastic bridge comprises first and second intersecting rods and have upper ends attached at diametrically opposite ends of the first annulus and lower ends attached to diametrically opposite ends of the second annulus wherein the first and second intersecting rods intersect at a pivot point configured to bring the upper ends closer together when the lower ends are brought closer together to reduce the outermost dimension of the first annulus when the outermost dimension of the second annulus is reduced;
    compressing the second annulus to pivot the first and second intersecting rods at the pivot point to bring the upper ends and lower ends of the rods, respectively, closer together and to reduce the outermost dimension of the first annulus to allow insertion of the pessary into the vagina;

inserting the pessary such that the first annulus is proximate a cervix and the second annulus is proximate an opening of the vagina posterior to a mid-urethra; and
releasing the second annulus to allow the first and second annuli to expand and the first and second annulus to contact the opposing walls of the vagina.

13. The method of claim 12 wherein a length of the first and second intersecting rods is between 4 cm and 9 cm.

14. The method of claim 12 wherein the second annulus is positioned posterior to the mid-urethra to provide an opposing force when pressure is applied to the mid-urethra.

15. The method of claim 12 wherein compressing the at least one of the first annulus, second annulus and the elastic bridge reduces a width of the pessary by at least 50% under less than 40 Newton force.

16. The method of claim 12 wherein an uncompressed diameter of the second annulus is less than the first annulus.

17. The method of claim 16 wherein the diameter of the first annulus is between 3 cm and 6 cm and a diameter of the second annulus is between 1 cm and 3 cm.

* * * * *